US012569633B2

(12) United States Patent
Trivikram

(10) Patent No.: US 12,569,633 B2
(45) Date of Patent: Mar. 10, 2026

(54) OSCILLATORY RESPIRATORY CARE APPARATUS

(71) Applicant: ABM RESPIRATORY CARE PTE. LTD, Singapore (SG)

(72) Inventor: Trivikram, Bangalore (IN)

(73) Assignee: ABM RESPIRATORY CARE PTE. LTD, Singapore (SG)

( * ) Notice: Subject to any disclaimer, the term of this patent is extended or adjusted under 35 U.S.C. 154(b) by 287 days.

(21) Appl. No.: 18/085,299

(22) Filed: Dec. 20, 2022

(65) Prior Publication Data

US 2023/0263974 A1 Aug. 24, 2023

Related U.S. Application Data

(63) Continuation of application No. 16/078,571, filed as application No. PCT/IB2016/057201 on Nov. 30, 2016, now Pat. No. 11,529,478.

(30) Foreign Application Priority Data

Feb. 22, 2016 (IN) .............................. 201641006118

(51) Int. Cl.
A61M 16/00 (2006.01)
A61H 9/00 (2006.01)
(Continued)

(52) U.S. Cl.
CPC ....... *A61M 16/0006* (2014.02); *A61H 9/0078* (2013.01); *A61M 16/0009* (2014.02);
(Continued)

(58) Field of Classification Search
CPC .......... A61M 16/0006; A61M 16/0009; A61M 16/0066; A61M 16/202; A61H 9/0078
See application file for complete search history.

(56) References Cited

U.S. PATENT DOCUMENTS 3,794,026 A * 2/1974 Jacobs .................. A61M 25/04
128/207.15
3,940,064 A 2/1976 Takaoka
(Continued)

FOREIGN PATENT DOCUMENTS

DE 00946258 7/1956
JP S57-190569 11/1892
(Continued)

OTHER PUBLICATIONS

EP Extended European Search Report in International Appln. No. 16891343, dated Oct. 22, 2019, 7 pages.
(Continued)

*Primary Examiner* — Kathryn E Ditmer
(74) *Attorney, Agent, or Firm* — Fish & Richardson P.C.

(57) ABSTRACT

Described herein is a respiratory care apparatus capable of performing multitude of therapy for secretion management and breath assistance therapy. The respiratory care apparatus comprises an electromechanical air router assembly (EARA) and an interfacing assembly. The EARA includes independent first and second pressure generating sources for assisted inhalation/insufflation and assisted exhalation/exsufflation process. The interfacing assembly includes a patient interface port and a patient interface tube. The interfacing assembly forms two pneumatically separate paths. The respiratory care apparatus is configured to generate alternate positive and negative pressure at the patient interface port for assisted inhalation/insufflation and assisted exhalation/exsufflation processes respectively. The assisted inhalation/insufflation and assisted exhalation/exsufflation processes are carried out independently through separate conduits/passages to reduce contamination and infection. Further, the respiratory care apparatus comprises a garment
(Continued)

which oscillates due to alternate positive and negative pressure generation and provides therapy to the patient.

16 Claims, 13 Drawing Sheets

(51) Int. Cl.

| | |
|---|---|
| *A61M 15/00* | (2006.01) |
| *A61M 16/06* | (2006.01) |
| *A61M 16/20* | (2006.01) |

(52) U.S. Cl.

CPC ...... *A61M 16/0066* (2013.01); *A61M 16/202* (2014.02); *A61H 2201/1619* (2013.01); *A61H 2201/165* (2013.01); *A61H 2201/501* (2013.01); *A61M 15/00* (2013.01); *A61M 2016/0027* (2013.01); *A61M 2016/003* (2013.01); *A61M 2016/0033* (2013.01); *A61M 16/06* (2013.01); *A61M 2205/3368* (2013.01); *A61M 2205/3592* (2013.01); *A61M 2205/50* (2013.01); *A61M 2205/7509* (2013.01); *A61M 2205/7518* (2013.01)

(56) References Cited

U.S. PATENT DOCUMENTS

| | | | | |
|---|---|---|---|---|
| 4,565,194 A | * | 1/1986 | Weerda | A61M 16/00 |
| | | | | 128/207.15 |
| 4,838,263 A | | 6/1989 | Warwick et al. | |
| 4,967,744 A | | 11/1990 | Chua | |
| 4,982,735 A | * | 1/1991 | Yagata | A61M 16/0677 |
| | | | | 128/204.23 |
| 5,056,505 A | * | 10/1991 | Warwick | A61M 16/0006 |
| | | | | 601/44 |
| 5,492,108 A | | 2/1996 | Smith et al. | |
| 5,829,428 A | | 11/1998 | Walters et al. | |
| 5,954,051 A | | 9/1999 | Heinonen et al. | |
| 5,988,166 A | * | 11/1999 | Hayek | A61M 16/20 |
| | | | | 601/48 |
| 6,041,777 A | | 3/2000 | Faithfull et al. | |
| 6,182,656 B1 | * | 2/2001 | Sagiv | A61H 31/02 |
| | | | | 128/202.12 |
| 6,209,540 B1 | | 4/2001 | Sugiura et al. | |
| 6,210,345 B1 | | 4/2001 | Van Brunt | |
| 6,237,589 B1 | | 5/2001 | Denyer et al. | |
| 6,789,540 B1 | * | 9/2004 | Lin | A61M 16/00 |
| | | | | 128/205.24 |
| 7,077,131 B2 | * | 7/2006 | Hansen | A61M 16/026 |
| | | | | 128/204.22 |
| 10,512,749 B2 | | 12/2019 | Lurie et al. | |
| 10,946,164 B2 | | 3/2021 | Lindstrom et al. | |
| 2003/0075176 A1 | * | 4/2003 | Fukunaga | A61M 16/08 |
| | | | | 128/911 |
| 2005/0031322 A1 | | 2/2005 | Boyle et al. | |
| 2005/0229928 A1 | | 10/2005 | Ivri et al. | |
| 2007/0199566 A1 | * | 8/2007 | Be'eri | A61M 16/024 |
| | | | | 128/204.23 |

| | | | | |
|---|---|---|---|---|
| 2010/0319691 A1 | * | 12/2010 | Lurie | A61M 16/04 |
| | | | | 128/205.24 |
| 2011/0073107 A1 | | 3/2011 | Rodman et al. | |
| 2012/0145153 A1 | * | 6/2012 | Bassin | A61M 16/0069 |
| | | | | 128/204.23 |
| 2013/0060157 A1 | | 3/2013 | Beard | |
| 2013/0092167 A1 | | 4/2013 | Perlman | |
| 2013/0150760 A1 | | 6/2013 | Flood | |
| 2014/0005566 A1 | | 1/2014 | Homuth et al. | |
| 2014/0116441 A1 | * | 5/2014 | McDaniel | A61M 16/0465 |
| | | | | 128/205.24 |
| 2014/0290659 A1 | * | 10/2014 | Chen | A61M 16/0006 |
| | | | | 128/205.24 |
| 2014/0373844 A1 | | 12/2014 | Brand et al. | |
| 2015/0027444 A1 | * | 1/2015 | Col, Jr. | A61M 16/0069 |
| | | | | 128/204.21 |
| 2015/0112707 A1 | | 4/2015 | Manice et al. | |
| 2015/0165144 A1 | * | 6/2015 | Lee | A61M 16/0003 |
| | | | | 128/204.23 |
| 2015/0238724 A1 | * | 8/2015 | Lindstrom | A61M 16/0096 |
| | | | | 128/204.21 |
| 2016/0022954 A1 | * | 1/2016 | Bath | A61B 5/0816 |
| | | | | 128/203.12 |
| 2016/0193438 A1 | * | 7/2016 | White | A61M 16/026 |
| | | | | 128/204.23 |
| 2016/0287819 A1 | * | 10/2016 | Greenblatt | A61M 16/0057 |
| 2017/0027813 A1 | * | 2/2017 | Bobey | A61H 9/0078 |
| 2017/0368410 A1 | * | 12/2017 | Brand | A61B 5/0823 |
| 2018/0104426 A1 | * | 4/2018 | Oldfield | A61M 16/024 |

FOREIGN PATENT DOCUMENTS

| | | |
|---|---|---|
| JP | H11-276588 | 10/1999 |
| JP | 2000-501306 | 2/2000 |
| JP | 2000-511093 | 8/2000 |
| JP | 2002-291889 | 10/2002 |
| JP | 2004-500905 | 1/2004 |
| JP | 2004-283329 | 10/2004 |
| JP | 2007-501074 | 1/2007 |
| JP | 2009-509610 | 3/2009 |
| JP | 2012-509148 | 4/2012 |
| JP | 2012-530556 | 12/2012 |
| JP | 2015-529134 | 10/2015 |
| WO | WO 2007054829 | 5/2007 |
| WO | WO 2012085792 | 6/2012 |
| WO | WO 2014111832 | 7/2014 |

OTHER PUBLICATIONS

JP Office Action in Japanese Appln. No. 2018562728, dated Jan. 15, 2021, 15 pages (with English translation).

JP Search Report in Japanese Appln. No. 2018562728, dated Nov. 30, 2020, 48 pages (with English translation).

PCT International Search Report and Written Opinion in International Application No. PCT/IB2016/057201, dated Jan. 29, 2018, 26 pages.

PCT Preliminary Report on Patentability in International Application PCT/IB2016/057201, dated Aug. 2, 2018, 25 pages.

\* cited by examiner

200

200

260

288

246

210

290

292

200

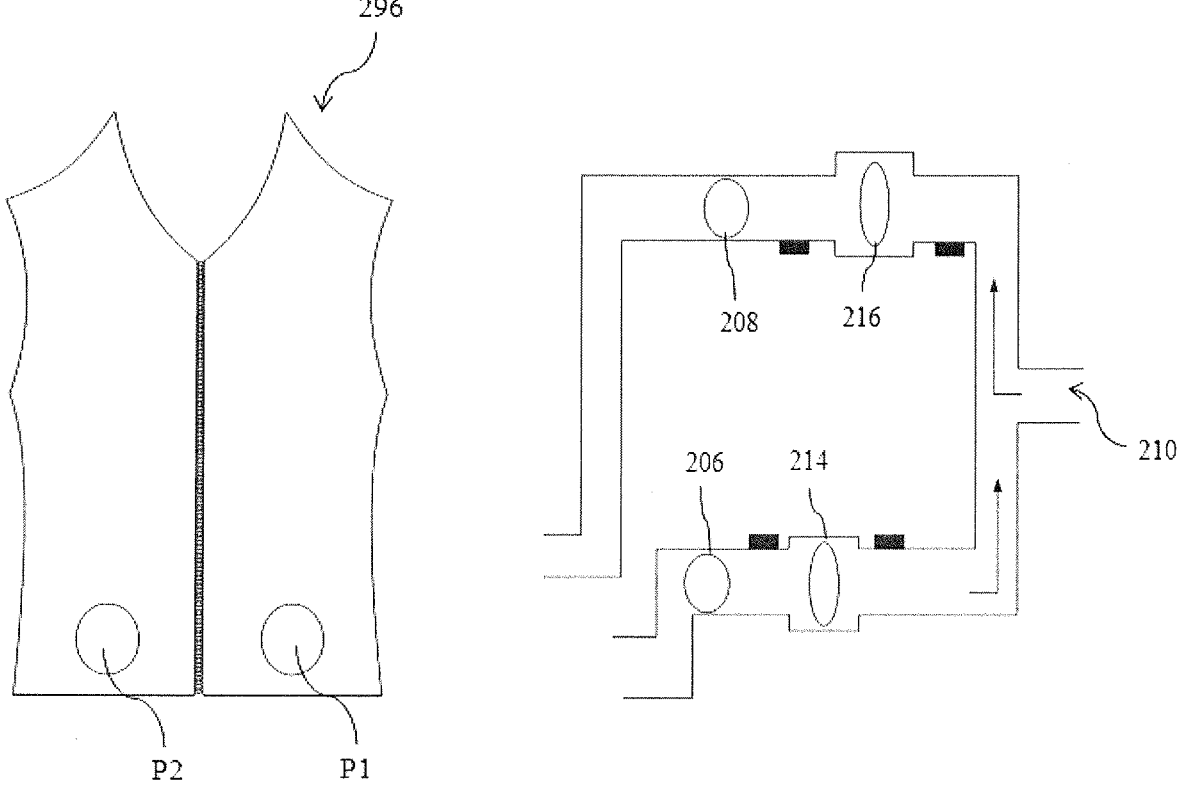
FIG. 15a                                FIG. 15b

OSCILLATORY RESPIRATORY CARE APPARATUS

CROSS-REFERENCE TO RELATED APPLICATIONS

This application continuation of U.S. patent application Ser. No. 16/078,571, filed on Aug. 21, 2018, which is a National Stage application under 35 U.S.C. § 371 of International Application No. PCT/IB2016/057201, filed Nov. 30, 2016, which claims the benefit of Indian Application No. 201641006118, filed on Feb. 22, 2016. The disclosures of the prior applications are incorporated by reference in their entirety.

TECHNICAL FIELD

The present subject matter relates to a medical device in general, and in particular, to a respiratory care apparatus which can be programmed and controlled with various configurations to provide lung ventilation and helps to manage airway secretion.

BACKGROUND

Patients having lung related diseases are unable to ventilate their lungs properly and may also suffer mucus clearance issues. This may happen when the normal lung defense system is damaged by lung related diseases.

Respiratory system is a complex structure which starts with upper airways, i.e. nose followed by trachea which branches into bronchus. The bronchus supplies air to the right and left lungs. Air splits progressively into the secondary and tertiary bronchi for the lobes of the lungs, and into smaller bronchioles to reach the respiratory bronchioles. The respiratory bronchioles in turn supply air through alveolar ducts into the alveoli, where the exchange of gases takes place.

As lungs are the only internal organs which get exposed to external environment, they act as a natural cleaning mechanism. Normally, lungs secrete mucus which traps dust and foreign particles. This mucus is moved upwards by tiny beating cells (cilia) to the main airways. If the quantity of mucus is more, one feels an urge to cough, otherwise this mucus is swallowed as part of Mucociliary Clearance mechanism continuously.

Hence, it is essential that this system works constantly to keep airway clean in order to have a healthy lung. Airway is kept clean by an effective airflow, "Mucociliary" clearance (MCC) and by an effective cough.

If either of "Mucociliary" clearance (MCC) and effective cough system is impaired or the lungs produce abnormal amount of mucus which cannot be handled by this system, then the mucus accumulates over a long run, thereby causing a collapse of alveoli (atelectasis). This also results in retaining of all the bacteria and dust inside the lungs causing a vicious cycle of illnesses.

Ineffective mucociliary clearance can happen either because of acquired causes such as post-infectious states (bacterial and viral pulmonary infections), bronchiectasis, lung transplantation, post-operative immobility, or because of congenital issues.

Mucociliary clearance is generally managed either by manual therapies such as chest physiotherapy, breathing exercises, physical exercises, or through various patient positioning techniques. Even though these techniques are efficacious, these kind of manual therapies are not only time consuming and labor intensive but also diminish patient's autonomy, eventually resulting in non-compliance of aforesaid mucociliary clearance regime.

Recently, there has been a significant advancement in airway clearance therapy either due to mechanical assisted/automated airway therapy modalities or due to better understanding of the disease profile. Mechanical/machine assisted airway clearance techniques fall under two categories, i.e. Active Airway Clearance Devices and Passive Airway Clarence Devices.

Passive airway clearance devices have shown to be efficacious in many instances. However, these devices are patient effort dependent as these are passive in nature. Therapy efficacy will be in question if a patient is not exerting enough flow during the respiration. Hence, the therapy may not yield the desired results as many of these patients are already very weak because of compromised lungs.

Active airway clearance devices, where external devices assist a patient to provide the therapies without much interference from the patient, are finding increasing applications in mucociliary clearance. High Frequency Chest Wall Oscillation (HFCWO) through external means (through chest wall) and oscillations through direct airways interface i.e. through mouthpiece or face mask are few categories of treatments available in active airway clearance space.

HFCWO devices provide high frequency chest wall oscillations, which help patients to mobilize their mucus from lower airways to upper airways. Few conventional devices work on the principle of a blower to generate a positive air pressure and a secondary module to oscillate the pressurized air inside a control box. The user wears a vest garment that contains an inflatable bladder connected to a control unit for rapid inflation and deflation. Further, some conventional devices generate the required chest wall oscillation through a vibratory/oscillatory mechanism using off-set motor coils directly inside the garment, instead of pumping air from a separate control box. These types of devices are used mainly by patients, who have issues with mucociliary clearance, such as CF. Bronchiectasis, etc., either through a separate control unit or the control unit attached to chest garment itself.

Intrapulmonary percussion devices are also known in the art, which deliver bursts of positive air to patient's direct airway through a mask/mouth piece/trachea tube, and the like. These devices simultaneously deliver an aerosolized medication. Similarly, there are other devices which provide a similar therapy with an additional CPEP function. More often, these kind of devices are pneumatic in nature and required high pressure O2 or airline.

Generally, patients who have neuromuscular issues such as ineffective glottis closure, impaired diaphragm movement or weak respiratory muscles are in need of mechanical assisted cough devices, i.e. mechanical Insufflation/Exsufflation. There are devices known in the art which provide solution in this category. For example, M-E devices mimic/simulate the cough function, typically, for those patients who have a peak airflow lesser than 270 liters per minute, by providing a positive pressure air and suddenly creating a negative pressure inside the lung, which in turn brings the mucus along the upper airways. M-E devices may also find their application in patients who have upper airway clearance issues after surgery, for example.

Airway clearance modalities include mobilization/move mucus/mucociliary clearance and mucus evacuation. Mobilization/move mucus/mucociliary clearance technique includes manual therapies such as CPT, bronchial drainage, physiotherapy, exercise, etc. and mechanical/device assisted therapies. The mechanical/device assisted therapies are further divided into passive devices and active devices through external means/garment attached to a patient's chest or with mouth interface/direct airway interface. The mucus evacuation, on the other hand, utilizes invasive devices, such as suction devices and bronchoscopy, as well as non-invasive/mechanical cough (M-IE) devices.

In hospitals, therapists generally need multiple airway clearance devices as patient's lung condition may require mucociliary clearance/airway mobilization or airway evacuation/assisted cough treatment or both. Firstly, the therapists have to ensure that the device does not introduce infection to the patients because of a possible ineffective infection control. Secondly, the therapists should manage and maintain multiple devices from various manufacturers. Thirdly, multiple devices impose huge strain on caregivers in terms of usability, Storage, learning, etc. Lastly, purchasing multiple devices involves high cost.

Similarly, in home settings, many patients are in need of multiple airway clearance devices. In such situations too, current treatment modalities have certain limitations, such as infection control (re-contamination at large and some cases cross contamination if they patients use serviced units), re-imbursement, flexibility and usability.

Devices which interact directly with patient interface impose huge risk in terms of cross contamination and re-contamination. In addition to typical infection control protocols such as cleaning/disinfecting the surface of the device and changing the patient circuit among patients, it is also critical that the device manufacturer ensures enough safety mitigation inside the control unit as well.

In home settings too, same risk profile applies except the fact that the device may impose higher risk of re-contamination. In addition, device manufacturers may service/repair the old/used units at their service line and send the used units to new patients. It is very important that the serviced units are free of contaminants too in order to help to reduce the cross contamination to new patient.

The existing airway clearance therapy devices use same airway channel/path inside the control unit for both Insufflation and Exsufflation purpose. Even though, such devices use a bacterial filter, there is always a possibility that the contaminants may enter the control unit. However, the control unit construction is not optimal to reduce infection as inhalation and exhalation paths are not isolated inside the device. It is also important to know the fact that the cough therapy is more intense than the typical ventilator, and hence it is important that the cough devices should use in-built design mitigation techniques to avoid cross contamination inside the control unit.

Further, as discussed before, hospitals, patients and/or caregivers need to purchase multiple devices if they need more than one kind of airway clearance modalities. It is really helpful if one device is able to perform multitude of airway clearance functions in one footprint. This will not only bring down the cost, but it also enhance the serviceability, portability and usability of the product.

In general, the existing airway clearance devices provide an internal gas source as either internal blowers, turbines or some form of pumps.

Out of the aforesaid devices, dual limb ventilation devices provide a patient circuit which has a dedicated limb for inspiratory gases or the gases going towards the lung and expiratory gases coming out of the lung. Such devices provide an internal positive pressure source while the expiration phase from the lung or external load is passive i.e. low is generated by recoil of elastic lung and chest wall.

Other devices like cough assist or single limb ventilators or intermittent oscillatory ventilators again have a single core internal pressure source (turbine, blower or other forms of pumps) and may generate a negative pressure (in case of cough assist) using a valve and manifold design, which changes the direction of pressure flow outlets mechanically using valves and other actuating mechanisms.

The feedback for the valves and pressure control is generated using sensors (flow, pressure, hall, encoder, temperature etc.) along the aforesaid pneumatic/airway path.

A basic actuating pump which has piston or fan/rotating blades and which generates flow and pressure by actuation of these flow creating mechanisms can generate flow or pressure only in one direction at a given time.

In addition to clinical challenges, the aforementioned therapy devices further face a basic issue of consuming expired gases into same pneumatic path and back into blower and valves, thereby contaminating them. The same air path is then used to provide inspiratory gas to the lung. Typically, the contamination risk to device is handled by placing a bacterial filter on the patient circuit. But in care scenarios at home where the filter may get wet or reused too many times, the device pneumatics have high probability of getting contaminated. Once the internal pneumatic paths are contaminated, it is very difficult to clean the pneumatic paths.

Apart from this, a single core pressure source with a valve manifold combination also creates constraints for response and control of pressure and flow in both directions.

Hence, there is a need for a respiratory care apparatus which overcomes the aforementioned and other related challenges.

SUMMARY

An object of the present subject matter is to provide a multitude of airway clearance modalities along with provision for contamination reduction.

Another object of the present subject matter is to provide separate conduits for insufflation/inhalation and exsufflation/exhalation to reduce contamination.

Yet another object of the present subject matter is to provide at least one positive pressure generating source.

Yet another object of the present subject matter is to provide at least one negative pressure generating source.

Yet another object of the present subject matter is to provide a first pressure restricting valve corresponding to the positive pressure generating source.

Yet another object of the present subject matter is to provide a second pressure generating source corresponding to the negative pressure generating source.

Yet another object of the present subject matter is to provide High Frequency Chest Wall Oscillation (HFCWO) therapy through a patient garment.

Yet another object of the present subject matter is to provide mechanical insufflation/exsufflation.

Yet another objection of the present subject matter is to provide nebulization therapy.

Yet another object of the present subject matter is to provide a connectivity module to transfer data.

The respiratory care apparatus according to the present subject matter encompasses embodiments, which not only address key clinical need with state of the art therapy features but also solves the challenges such as precise pressure controls, infection risk and portability. Further, the present disclosure addresses the key concerns related to flexibility of airway clearance therapies.

The present disclosure comprises at least one first pressure generating source and at least one second pressure generating source. The at least one first pressure generating source and the at least one second pressure generating source are configured to function independently with respect to each other. These said independent pressure generating sources are configured to generate flow and pressure continuously in opposite as well as same direction.

The respiratory care apparatus further comprises a first pressure restricting valve, a second pressure restricting valve, at least one patient interface port and a manifold structure. A first pneumatic/airway path is formed between the at least one first pressure generating source and the at least one patient interface port. A second pneumatic/airway path is formed between the at least one second pressure generating source and the at least one patient interface port. One of the said pneumatic paths is configured to be used as one way inspiratory path while the other path is configured to be used only for negative pressure and flow from the lung (exhalation). Thus, a clean inspiratory path to external load or lung is formed which is least affected against contamination through gas flowing back from the external load or from lung or from patient interface.

In an embodiment, the respiratory care apparatus comprises an electronic air router assembly (EARA). The EARA is capable of providing multiple airway clearance therapy portably. The EARA can be configured (through hardware/mechanical, software and interfacing assembly) in order to deliver various airway clearance therapies.

In another embodiment, the respiratory care apparatus comprises a connectivity module configured for two way data transfer/communication. The connectivity module is based on LTE (Long Term Evolution) and GSM (Global System for Mobile Communications). The data transferred from the respiratory care apparatus through the connectivity module comprises one or more of at delivered pressure, flow, pressure/flow related graphs and the corresponding user parameters. The data transferred from the respiratory care apparatus further comprises one or more of total device usage data, prescribed total therapy protocol, sensor data such as $SpO2$ and respiratory rate. The prescribed total therapy protocol comprises parameters such as possible pressure settings oscillation settings, duration of therapy and number of therapies.

The present subject matter relates to a respiratory care apparatus comprising an interfacing assembly having separate conduits for inhalation and exhalation. The interfacing assembly comprises at least one patient interface port and a patient interface tube having a first end and a second end. The first end of the patient interface tube is connected with the at least one patient interface port. The second end of the patient interface tube is connected with one or more of a face mask, mouth piece, artificial lung tubing, tracheal tube adapter, expiratory resistance change adapter and ventilator interface adapter. The patients interface tube is tube-in-tube type having an outer conduit, an inner conduit and a collector chamber. The patient interface tube comprises separate conduits for inhalation and exhalation to reduce contamination. The interfacing assembly comprises a patient interface means, the patient interface means is in connection with patient's external garment. The respiratory care apparatus further comprises at least one first pressure generating source configured to generate flow and pressure and least one second pressure generating source configured to generate flow and pressure. The at least one conduit is formed between the at least one patient interface port, the at least one first pressure generating source and the at least one second pressure generating source.

In an embodiment, the present subject matter relates to a respiratory care apparatus comprising an interfacing assembly having separate conduits for inhalation and exhalation, at least one first pressure generating source configured to generate flow and pressure and at least one second pressure generating source configured to generate flow and pressure. The interfacing assembly comprises at least one patient interface port. The at least one first pressure generating source comprises an inlet which draws atmospheric air into the at least one first pressure generating source and an outlet which outputs air from the at least one first pressure generating source to the at least one patient interface port. The at least one second pressure generating source comprises an inlet which draws air from the at least one patient interface port into the at least one second pressure generating source and an outlet which outputs air to atmosphere. The at least one first pressure generating source and the at least one second pressure generating device are configured to function independently with respect to each other.

In another embodiment, the present subject matter relates to a respiratory care apparatus comprising an interfacing assembly having separate conduits for inhalation and exhalation, a first pressure restricting valve configured to control pressure and/or flow and a second pressure restricting valve configured to control pressure and/or flow. The interfacing assembly comprises a patient interface port. The respiratory care apparatus further comprises at least one first pressure generating source configured to generate flow and pressure and at least one second pressure generating source configured to generate flow and pressure. The first pressure restricting valve is disposed between the at least one first pressure generating source and the at least one patient interface port. The first pressure restricting valve is configured to control pressure between the at least one first pressure generating source and the at least one patient interface port. The second pressure restricting valve is disposed between the at least one second pressure generating source and the at least one patient interface port. The second pressure restricting valve is configured to control pressure between the at least one second pressure generating source and the at least one patient interface port. The first pressure restricting valve comprises a first electromechanical valve structure housed in a hollow structure having a first port and a second port. The first port is pneumatically connected to outlet of the at least one first pressure generating source and the second port is pneumatically connected to the at least one patient interface port. The first electromechanical valve structure is controlled bi-directionally through displacement of a first electromechanical motor. The second pressure restricting valve comprises a second electromechanical valve structure housed in a hollow structure having a first port and a second port. The first port is pneumatically connected to the at least one patient interface port and the second port is pneumatically connected to inlet of the at least one second pressure generating source. The second electromechanical valve structure is controlled bi-directionally through displacement of a second electromechanical motor.

In yet another embodiment, the present subject matter relates to a respiratory care apparatus comprising an interfacing assembly having separate conduits for inhalation and exhalation and an electromechanical air router assembly. The electromechanical air router assembly comprises at least one first pressure generating source. The electromechanical air router assembly comprises at least one second pressure generating source. The at least one first pressure generating source comprises an inlet and an outlet. The at least one second pressure generating source comprises an inlet and an outlet. The electromechanical air router assembly comprises a first electromechanical valve structure. The electrome- chanical air router assembly comprises a second electrome- chanical valve structure. The first electromechanical valve structure is in pneumatic connection with the atmosphere through the first pressure generating source. The first elec- tromechanical valve structure is disposed in proximity with the outlet of the first pressure generating source. The first electromechanical valve structure is in connection with the interfacing assembly through a manifold/air router structure. The second electromechanical valve structure is in pneu- matic connection with the atmosphere through the second pressure generating source. The second electromechanical valve structure is disposed in proximity with the inlet of the second pressure generating source. The second electrome- chanical valve structure is in connection with the interfacing assembly through the manifold/air router structure. The first pressure generating source is separately connected to the interfacing assembly via the manifold/air router structure. The second pressure generating source is separately con- nected to the interfacing assembly via the manifold/air router structure. The electromechanical air router assembly is configured to provide separate inhalation and exhalation paths through the manifold/air router structure and the interfacing assembly.

In yet another embodiment, the present subject matter relates to a respiratory care apparatus comprising an inter- facing assembly having separate conduits for inhalation and exhalation, at least one first pressure generating source configured to generate flow and pressure, at least one second pressure generating source configured to generate flow and pressure, a first pressure restricting valve configured to control pressure and a second pressure restricting valve configured to control pressure. The at least one second pressure generating source is blocked using the second pressure restricting valve and the speed of the first pressure generating source is controlled in synchronization with the first pressure restricting valve. The pressure is set to a value based on set parameters and the feedback from one or more sensing parameters such as a pressure sensor, encoder, flow sensor, and temperature sensor to create positive pressure at the at least one patient interface port. The at least one first pressure generating source is blocked using the first pressure restricting valve and the speed of the at least one second pressure generating source is controlled in synchronization with the second pressure restricting valve. The pressure is set to a value based on set parameters and the feedback from one or more sensing parameters such as a pressure sensor, a flow sensor, a hall sensor, encoder, and temperature sensor, to create negative pressure at the at least one patient inter- face port. The at least one second pressure generating source is blocked using the second pressure generating structure and the speed of the at least one first pressure generating source is varied to generate oscillating waveform at the at least one patient interface port. The first pressure restricting valve is adjusted to generate positive waveform having a first amplitude value. The first pressure restricting valve is adjusted to generate a positive pressure having a second amplitude value. The oscillating pressure waveform is gen- erated based on user set parameters such as oscillation amplitude and oscillation pressure. The pressure is con- trolled based on set parameters and the feedback from one or more sensors such as pressure sensor, flow sensor, encoder, hall sensor and temperature sensor. The positive waveforms are continuous or discrete in nature. The fre- quency of the positive waveforms varies between 0 to 50 Hz. The at least one first pressure generating source is blocked using the first pressure restricting valve and the speed of the at least one second pressure generating source is varied to generate oscillating waveform at the at least one patient interface port. The second pressure restricting valve is adjusted to generate negative waveform having a first ampli- tude value. The second pressure restricting valve is adjusted to generate a negative pressure having a second amplitude value. The oscillating pressure waveform is generated based on user set parameters such as oscillation amplitude and oscillation pressure. The pressure is controlled based on the feedback from one or more sensors such as pressure, flow, encoder, hall sensor and temperature sensor. The negative waveforms are continuous or discrete in nature. The fre- quency of the negative waveform varies between 0 to 50 Hz. The at least one patient interface port comprises nebulizer connecting port. The at least one patient interface port comprises sensor interfacing port. The respiratory care appa- ratus further comprises a bacterial filter and/or a viral filter for infection control. The respiratory care apparatus further comprises a built-in intelligence module configured to detect patient's breathing response to a frequency pressure wave- form. The said frequency range varies between 0 to 50 Hz. The intelligence module comprises microcontrollers and electronic components. The intelligence module is config- ured to process patient's response to oscillating waveform, the processing happens in time and frequency domain. The processed data is used to assess parameters such as patient's lung condition and therapy performance.

In yet another embodiment, the subject matter relates to a respiratory care apparatus comprising an interfacing assem- bly having separate conduits for inhalation and exhalation and a connectivity module configured to transfer data. The connectivity module is based on LTE (Long Term Evolu- tion) and GSM (Global System for Mobile Communica- tions). The data transferred from the respiratory care appa- ratus through the connectivity module comprises one or more of at delivered pressure, flow, pressure/flow related graphs and the corresponding user parameters. The data transferred from the respiratory care apparatus through the connectivity module comprises one or more of total device usage data, prescribed total therapy protocol, sensor data such as SpO2 and respiratory rate. The prescribed total therapy protocol comprises parameters such as possible pressure settings, oscillation settings, duration of therapy and number of therapies. The connectivity module com- prises a two way data communication. The two way data communication comprises notes from individual such as patients, caregivers and clinicians.

In yet another embodiment the present subject matter relates to a method for administering therapy to a patient using a respiratory care apparatus. The method comprising connecting an interfacing assembly, wherein the interfacing assembly has separate conduits for inhalation and exhalation to a patient. The method further comprises generating a positive pressure at the interfacing assembly for inhalation, generating a negative pressure at the interfacing assembly for exhalation, providing separate inhalation and exhalation paths to reduce cross contamination and infection, transfer- ring of patient data to caregiver and clinicians and transfer- ring prescribed total therapy protocol to the patient, wherein the prescribed total therapy protocol comprises one or more of parameters such as possible pressure settings, oscillation settings, duration of therapy and number of therapies. Also, the method comprises providing a nebulization therapy through an electric conduit to patient interface port.

In yet another embodiment, the present subject matter relates to a respiratory care apparatus comprising an interfacing assembly having separate conduits for inhalation and exhalation, at least one first pressure generating source configured to generate flow and pressure, at least one second pressure generating source configured to generate flow and pressure, at least one third pressure generating source to deliver the aerosolized medicine and a control mechanism to deliver nebulization in synchronization with assisted inhalation and assisted exhalation cycle of the patient. The synchronization includes electronic control of the at least one third pressure generating source at the same time with EARA operations. The at least one third pressure generating source is pneumatically driven. The at least one third pressure generating source is electrically driven.

In yet another embodiment, the present subject matter relates to a respiratory care apparatus comprising an interfacing assembly having separate conduits for inhalation and exhalation, at least one first pressure generating source configured to generate flow and pressure, at least one second pressure generating source configured to generate flow and pressure, at least one third pressure generating source to deliver the aerosolized medicine and at least two patient ports attached to a patient garment. The at least one second pressure generating source is blocked using the second pressure restricting valve and the speed of the at least one first pressure generating source is varied to generate positive oscillating waveform at the at least one patient interface port. The position of the first pressure restricting valve is altered continuously from a first position to a second position to generate positive oscillation waveform at the at least one patient interface port. The frequency of the positive waveforms varies between 0 to 50 Hz. The at least one first pressure generating source is blocked using the first pressure restricting valve and the speed of the at least one second pressure generating source is varied to generate negative oscillating waveform at the at least one patient interface port. The position of the second pressure restricting valve is altered continuously from a first position to a second position to generate negative oscillation waveform at the at least one patient interface port. The frequency of the negative waveform varies between 0 to 50 Hz. The first pressure restricting valve and the second pressure restricting valve can be used in synchronization with each other to generate oscillation simultaneously. The at least one first pressure generating source is unblocked using the first pressure restricting valve such that the position of the first pressure restricting valve is altered continuously from a first position to a second position. The at least one second pressure generating source is partially unblocked using the second pressure restricting valve such that the position of the second pressure restricting valve is altered continuously from a first position to a second position. The position of the first pressure restricting valve and the position of the second pressure restricting valve can be changed alternately to block/unblock the at least one first pressure generating source and the at least one second pressure generating source respectively to generate aggressive oscillation by forming alternate positive and negative waveforms. The respiratory care apparatus is configured to perform oscillation in the patient garment. The patient garment expands during positive pressure generation and contracts during the negative pressure generation. The patient garment oscillates due to alternate positive and negative pressure generation. The patient garment is configured to provide oscillation therapy to a patient.

BRIEF DESCRIPTION OF ACCOMPANYING DRAWINGS

A further understanding of the present subject matter can be obtained by reference to various embodiments set forth in the illustrations of the accompanying drawings. The drawings are not intended to limit the scope of the present subject matter, which is set forth with particularity in the claims as appended or as subsequently amended, but merely to clarify and exemplify the subject matter.

For a fuller understanding of the nature and object of the present subject matter, reference is made to the accompanying drawings, wherein.

Figure 1:
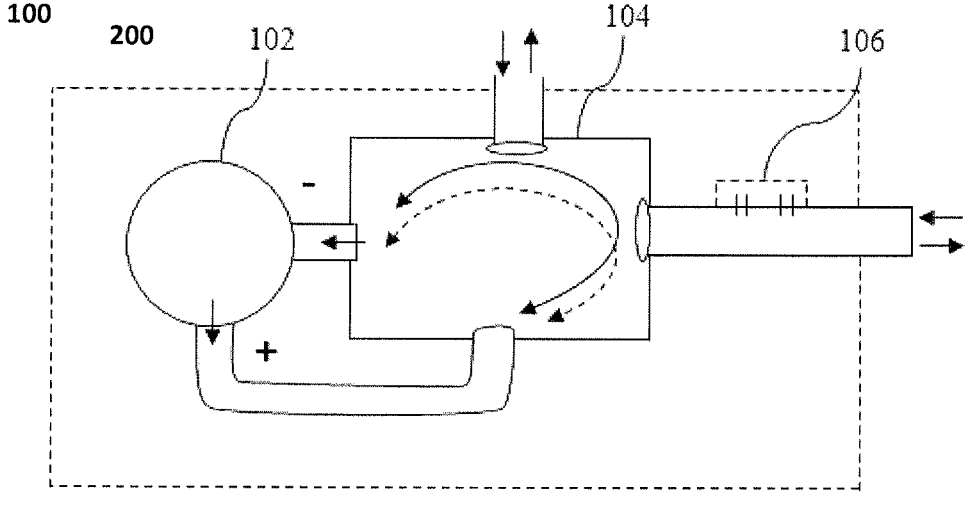
FIG. 1 is a schematic diagram illustrating working of a conventional airway clearance device.

FIG. 15*a* and FIG. 15*b* illustrate a schematic view of a patient garment and a pressure generation mechanism of the respiratory care apparatus for the patent garment respectively in accordance with an embodiment of the present subject matter.

DETAILED DESCRIPTION

The following presents a detailed description of various embodiments of the present subject matter with reference to the accompanying drawings.

As used herein, the singular forms "a". "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include operatively connected or coupled. As used herein, the term "and/or" includes any and all combinations and arrangements of one or more of the associated listed items.

The embodiments of the present subject matter are described in detail with reference to the accompanying drawings. However, the present subject matter is not limited to these embodiments which are only provided to explain more clearly the present subject matter to the ordinarily skilled in the art of the present disclosure. In the accompanying drawings, like reference numerals are used to indicate like components.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The detailed description set forth below in connection with the appended drawings is intended as a description of the several presently contemplated embodiments of a respiratory care apparatus. The apparatus is capable of providing multiple therapies for respiratory system, more specifically, for airway clearance. The apparatus can be configured to deliver various airway clearance therapies through hardware/mechanical, software and patient circuit configurations. The respiratory care apparatus comprises therapy capabilities including but not limiting to HFCWO (high frequency chest wall oscillation) therapy through an external chest garment, M-E (mechanical insufflation/exsufflation) therapy through a patient circuit, HFO/IPV (high frequency oscillation) therapy through a patient circuit, PAP (positive air pressure) through a patient circuit, Oscillating PAP through a patient circuit, suction through a patient circuit, CPAP (continuous positive air pressure) functions and Bi-PAP (bi-level positive air pressure) functions. This description is not intended to represent the only form in which the disclosed subject matter may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

FIG. 1 is a schematic diagram of a conventional airway clearance device 100 known in the art. The conventional airway clearance device 100 comprises dual limb ventilation and a patient circuit which has a dedicated limb for inspiratory gases or the gases going towards the lung and expiratory gases coming out of the lung. Such devices provide an internal positive pressure source 102 while the expiration phase from the lung or external load is passive i.e. flow is generated by recoil of lung and chest wall.

Other devices like cough assist or single limb ventilators or intermittent oscillatory ventilators also have a single core internal pressure source 102 like a turbine, blower or other forms of pumps and may generate a negative pressure (in case of cough assist) using a valve and a manifold 104 which changes the direction of pressure flow outlets mechanically using valves and other similar actuating mechanisms.

The feedback for the valves and pressure control is generated by a sensor 106 including but not limiting to pressure sensors and/or flow sensors.

Further, a single unit of basic actuating pump which has a piston or fan/rotating blades and which generates flow and pressure by actuation of flow creating mechanisms can be used as the core pressure source 102. However, the core pressure source 102 can generate flow and/or pressure only in one direction at a specific point in time.

Figure 2:
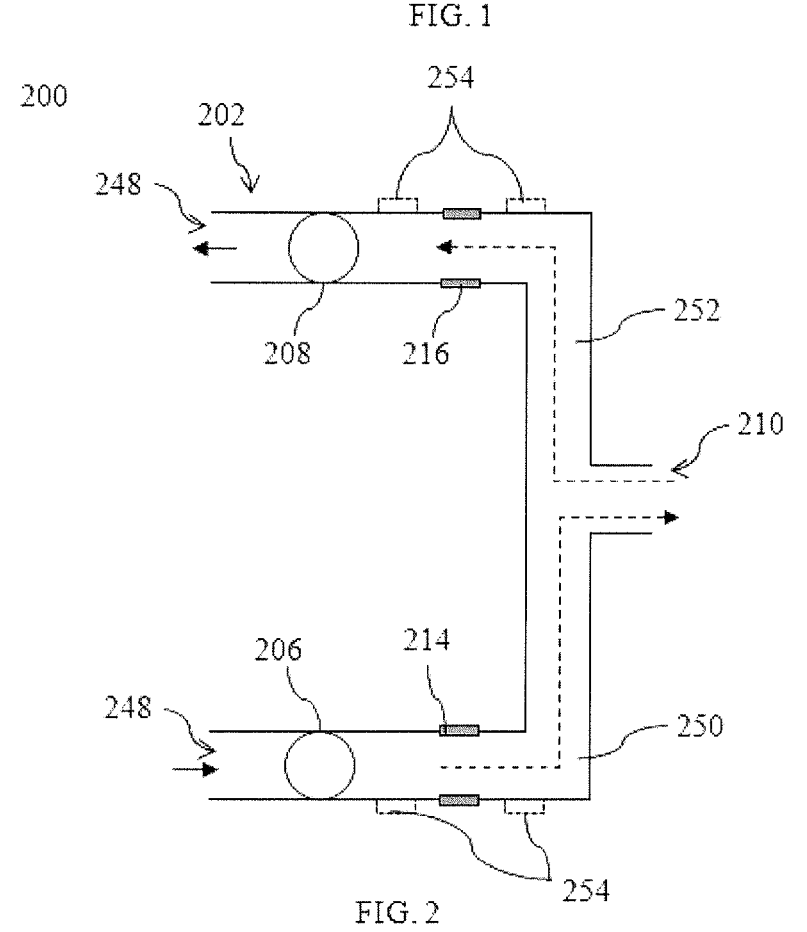
FIG. 2 is a schematic diagram illustrating an electromechanical airway router assembly of a respiratory care apparatus in accordance with an embodiment of the present subject matter.
Figure 12:
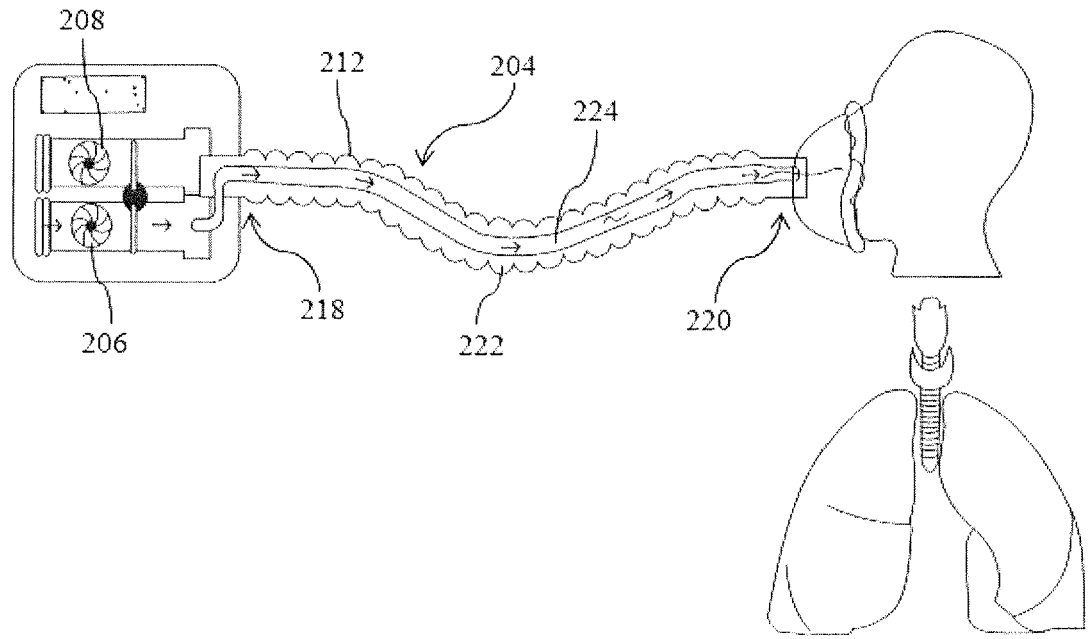
FIG. 12 is a schematic representation of a respiratory care apparatus showing a positive pressure generation and patient interface in accordance with an embodiment of the present subject matter.

FIG. 2 discloses a schematic diagram of respiratory care apparatus 200 in one embodiment of the present disclosure. The respiratory care apparatus 200 comprises a plurality of components including but not limiting to an electromechanical airway router assembly 202 and an interfacing assembly 204 (as shown in FIG. 12). The electromechanical airway router assembly 202 comprises at least one first pressure generating source 206 and at least one second pressure generating source 208. The interfacing assembly 204 comprises at least one patient interface port 210 and a patient interface tube 212. The patient interface tube 212 can be of tube-in-tube type or any other suitable type known in the art to provide separate conduits/passages for insufflation and exsufflation. The at least one second pressure generating source 208 is configured to generate flow and pressure. The aforesaid pressure generating sources can be chosen from blowers, turbines, pumps, and the like. However, it is evident to a person of ordinary skills in the art that the type of patient interface tube and the pressure generating sources used does not limit the scope of present disclosure. The at least one patient Interface port 210 forms a first conduit between the at least one interfacing assembly 204 and the at least one first pressure generating source 206, the at least one patient Interface port 210 forms a second conduit between the at least one interfacing assembly 204 and the at least one second pressure generating source 208. In other words, at least one pneumatic/airway path (conduit) is formed between each of the pressure generating sources 206, 208 and the at least one interfacing assembly 204. The at least one patient interface port 210 enables the formation of such pneumatic/airway path (conduit). The electromechanical air router assembly further comprises a first pressure restricting valve 214 and a second pressure restricting valve 216. The first pressure restricting valve 214 is disposed between the at least one interfacing assembly 204 and the at least one patient interface port 210. The first pressure restricting valve 214 is configured to control pressure between the at least one interfacing assembly 204 and the at least one patient interface port 210. Further, the second pressure restricting valve 216 is disposed between the at least one second pressure generating source 208 and the at least one patient interface port 210. The second pressure restricting valve 216 is configured to control pressure between the at least one second pressure generating source 208 and the at least one patient interface port 210. In an embodiment, the first and second pressure restricting valves 214, 218 are not limited to controlling pressure only. Moreover, the first and second pressure restricting valves 214, 218 can alter the pressure and flow with respect to the at least one first pressure generating source 206 and the at least one second pressure generating source 208 respectively.

Figure 5:
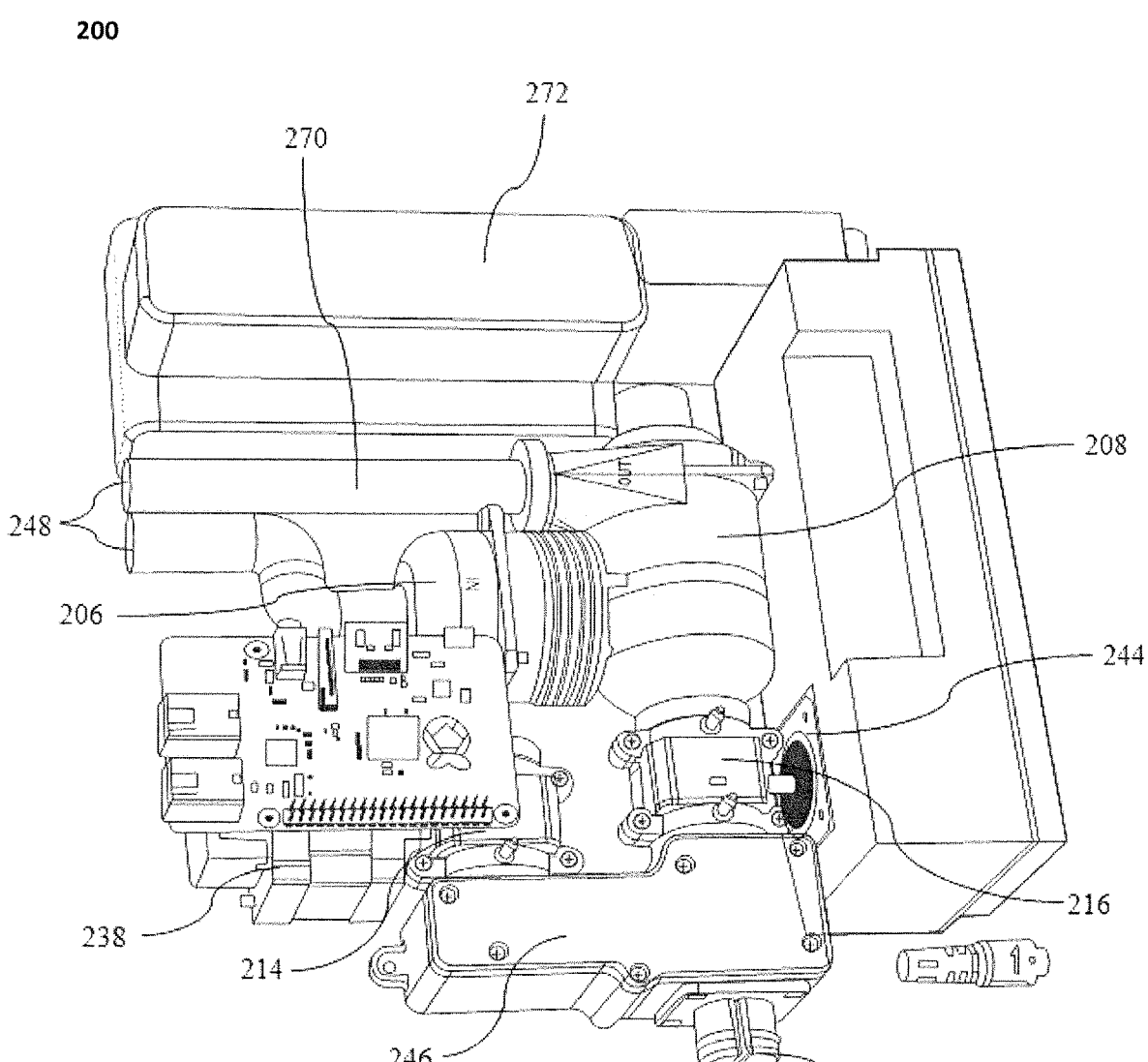
FIG. 5 is a three dimensional view of the internal components of a respiratory care apparatus in accordance with an embodiment of the present subject matter.
Figure 6:
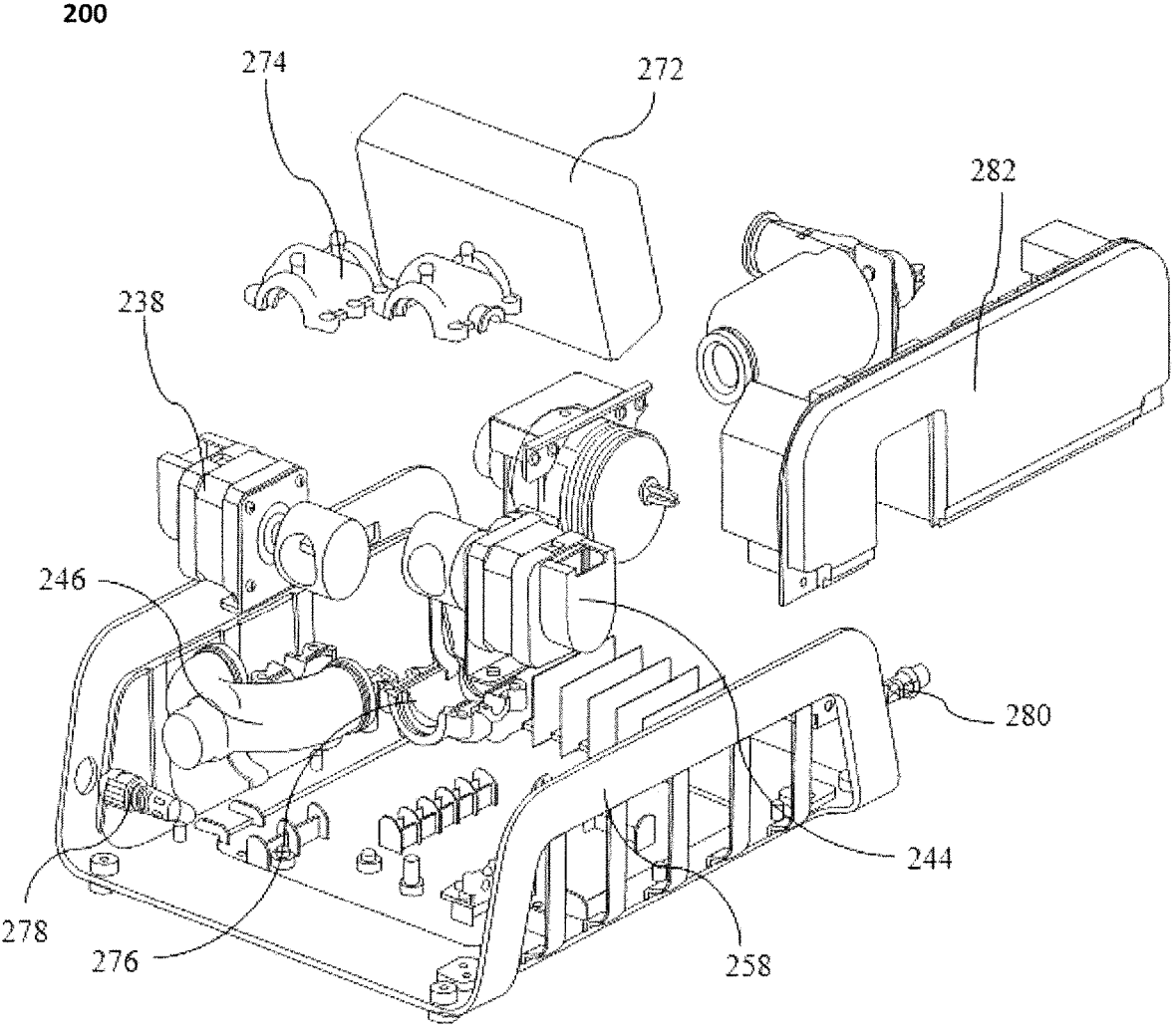
FIG. 6 illustrates an exploded view of a respiratory care apparatus in accordance with an embodiment of the present subject matter.
Figure 9:
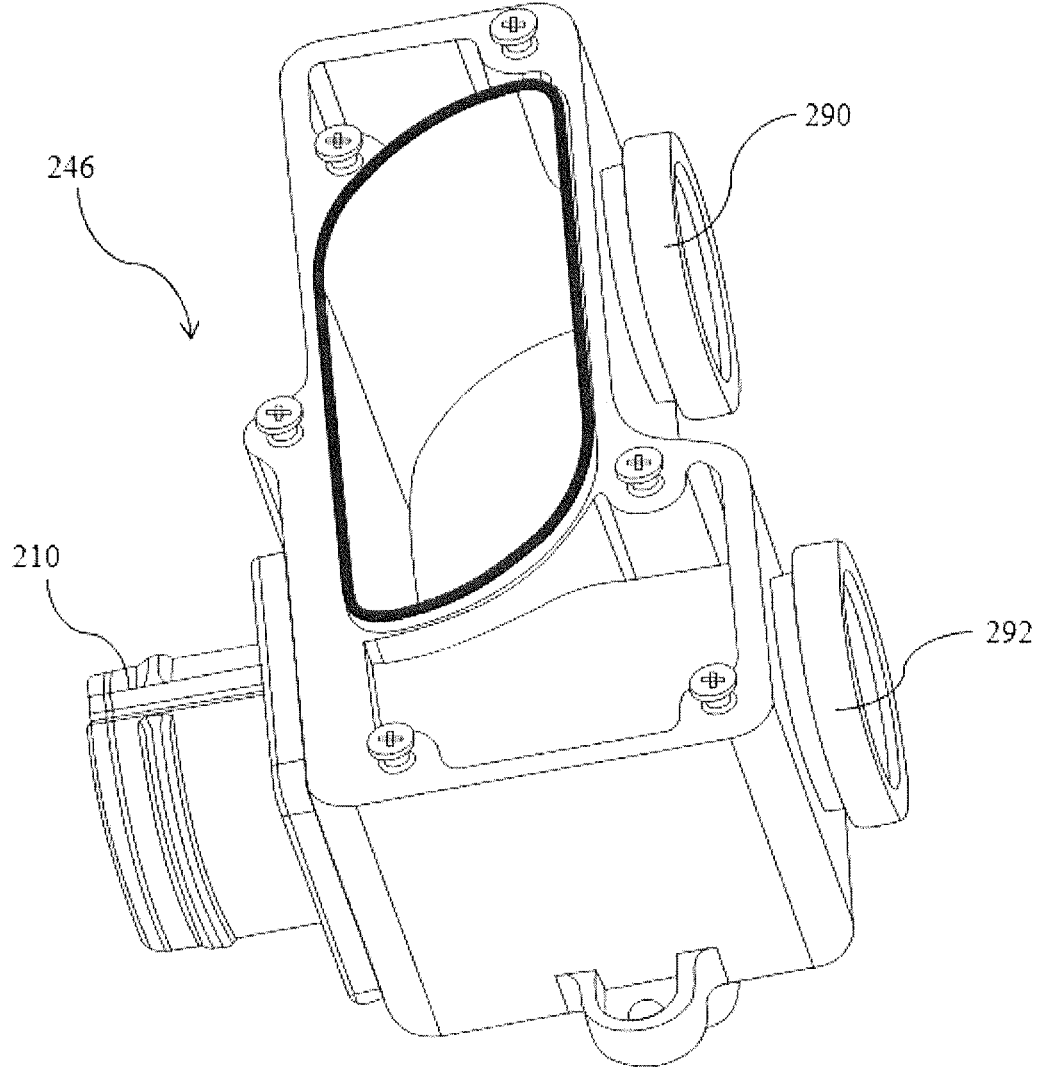
FIG. 9 illustrates a perspective view of a manifold/air router structure of the respiratory care apparatus in accordance with an embodiment of the present subject matter.

The respiratory care apparatus 200 further comprises a manifold/air router structure 246 (as shown in FIG. 5. FIG. 6 and FIG. 9). The manifold/air router structure 246 can be hollow cuboidal type, circular type, Y-shaped, cylindrical type or any other suitable manifold/air router structure 246 type known in the art. However, it is evident to a person of ordinary skills in the art that the type of manifold/air router structure 246 used does not limit the scope of the present disclosure. The first electromechanical valve structure is in pneumatic connection with the at least one patient interface port 210 of the interfacing assembly 204 through the manifold/air router structure 246. The first electromechanical valve structure is disposed in proximity with the outlet of the at least one interfacing assembly 204 such that the first electromechanical valve structure is in pneumatic connection with the atmosphere through the interfacing assembly 204. Further, the second electromechanical valve structure is in connection with the interfacing assembly 204 through the manifold/air router structure 246. The second electromechanical valve structure is disposed in proximity with the inlet of the at least one second pressure generating source 208 such that the second electromechanical valve structure is in pneumatic connection with the atmosphere through the at least one second pressure generating source 208. A plurality of atmospheric vents 248 is provided in the electromechanical airway router assembly 202 for connection with the atmosphere. Furthermore, the at least one interfacing assembly 204 and the at least one second pressure generating source 208 are separately connected to the interfacing assembly 204 via said manifold/air router structure 246. Hence, the electromechanical air router assembly is configured to provide separate inhalation and exhalation paths through the manifold/air router structure 246 and the interfacing assembly 204.

In an embodiment, the first pressure restricting valve 214 and the second pressure restricting valve 216 are electronic motor valves (EMVs). The purpose of the electronic motor valves is to allow the air from one pressure generating source at a time to reach the at least one patient interface port 210. Meantime, it is also important to control the pressure and the flow of the airway path for the at least one interfacing assembly 204 and the at least one second pressure generating source 208 through additional oscillation generation mechanism. There can be numerous valve constructions to be used in the respiratory care apparatus 200. For instance and by no way limiting the scope of the present disclosure the valve constructions may include air-pressure based diaphragm valve, DC motor valve, stepper motor valve, piezo-electric valve, and the like.

In an embodiment, a first pneumatic/airway path 250 corresponding to the at least one first pressure generating source 206 is created by the combination of the manifold/air router structure 246 and the first pressure restricting valve 214. Similarly, a second pneumatic/airway path 252 corresponding to the at least one second pressure generating source 208 is created by the combination of the manifold/air router structure 246 and the second pressure restricting valve 216. One of the pneumatic paths 250, 252 corresponds to inspiratory path while the other path would be only used for negative pressure and flow from the lung. Thus, a clean inspiratory path to external load or lungs is created without getting contaminated by gas flowing back from the external load or from lung or from any portion of the interfacing assembly 204. The electromechanical air router assembly 202 further comprises a plurality of sensors 254 for monitoring pressure at the patient interface port in real time.

Figure 3:
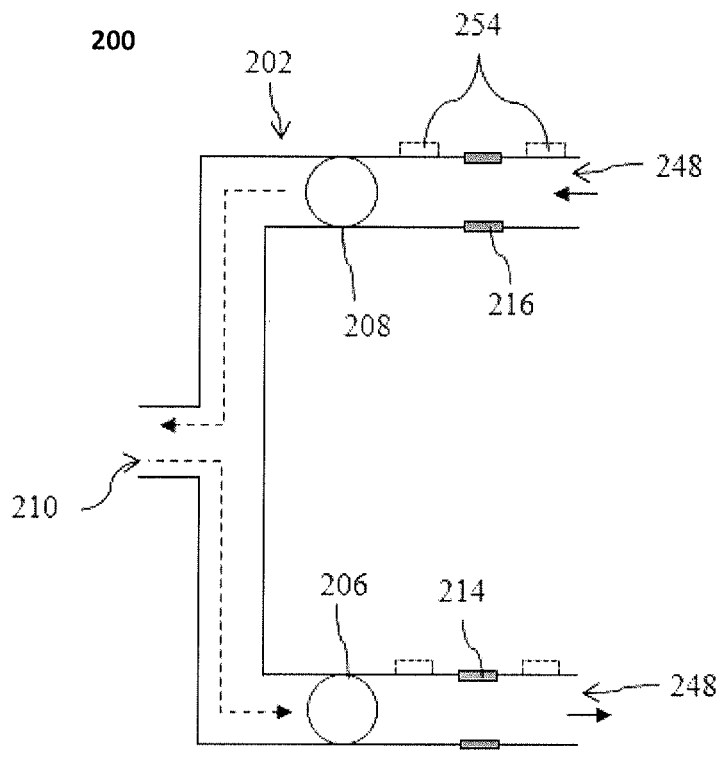
FIG. 3 is a schematic diagram illustrating an electromechanical airway router assembly of a respiratory care apparatus in accordance with another embodiment of the present subject matter.

In an embodiment, the patient interface port 210 and the plurality of atmospheric vents 248 can be reversed with respect to each other to get the similar effect. However, in this case the first pressure restricting valve 214 and the second pressure restricting valve 216 are positioned plurality of vents and the pressure generating sources, as shown in FIG. 3.

The at least one patient interface port 210 is connected with the patient interface tube 212. The patient interface tube 212 comprises a first end 218 and a second end 220 (shown in FIG. 12). The first end 218 of the patient interface tube 212 is connected with the at least one patient interface port 210 and the second end 220 of the patient interface tube 212 is connected with one or more of a face mask, mouth piece, artificial lung tubing, tracheal tube adapter, expiratory resistance change adapter and ventilator interface adapter.

In a preferred embodiment, the patient interface tube 212 is tube-in-tube type having an outer conduit 222, an inner conduit 224 and a collector chamber (not shown in figures). The outer conduit 222 can be used for inhalation/insufflation and the inner conduit 224 can be used for exhalation/exsufflation. In another embodiment, the outer conduit 222 can be used for exhalation/exsufflation and the inner conduit 224 can be used for inhalation/insufflation. The patient interface tube 212 comprises separate conduits for inhalation/insufflation and exhalation/exsufflation to reduce cross contamination and infection. The interfacing assembly 204 further comprises a patient interface means, the patient interface means (not shown in figures) is in connection with a patient's external garment to provide High Frequency Chest Wall Oscillation (HFCWO) therapy. The patient interface means and/or the patient interface tube 212 along with the at least one patient interface port 210 are fluidly connected with the at least one first pressure generating source 206 and the at least one second pressure generating source 208.

The at least one interfacing assembly 204 comprises an inlet in proximity with the first end 218 which draws atmospheric air into the at least one interfacing assembly 204 and an outlet in proximity with the second end 220 which outputs air from the at least one interfacing assembly 204 to the at least one patient interface port 210. Further, the at least one second pressure generating source 208 comprises an inlet which draws air from the at least one patient interface port 210 into the at least one second pressure generating source 208 and an outlet which outputs air to atmosphere. The at least one interfacing assembly 204 and the at least one second pressure generating device are configured to function independently with respect to each other. Both the aforesaid pressure generating sources are connected with separate paths (conduits) of the interfacing assembly 204 to reduce cross contamination and infection.

The pressure flow in respect of the at least one first pressure generating source and the at least one second pressure generating source is controlled by the first pressure restricting valve 214 and the second pressure restricting valve 216 respectively. The first pressure restricting valve 214 comprises a first electromechanical valve structure housed in a hollow structure having a first port and a second port. The first port is pneumatically connected to outlet of the at least one interfacing assembly 204 and the second port is pneumatically connected to the at least one patient interface port 210. The first electromechanical valve structure is controlled bi-directionally through general displacement motion of a first electromechanical motor 238.

Further, the second pressure restricting valve 216 comprises a second electromechanical valve structure housed in a hollow structure having a first port and a second port. The first port is pneumatically connected to the at least one patient interface port 210 and the second port is pneumatically connected to inlet of the at least one second pressure generating source 208. The second electromechanical valve structure is controlled bi-directionally through rotary motion of a second electromechanical motor 244.

Figure 4:
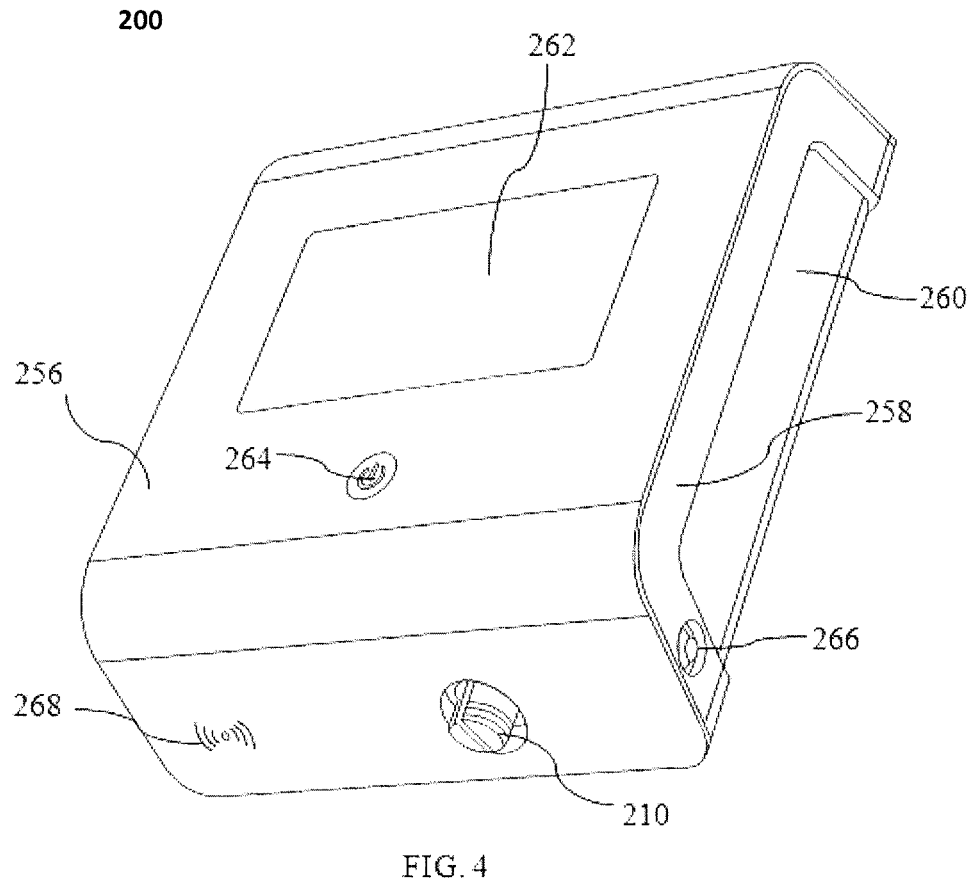
FIG. 4 is a perspective view of a respiratory care apparatus in accordance with an embodiment of the present subject matter.

Referring FIG. 4, a perspective view of the respiratory care apparatus 200 is illustrated in accordance with an embodiment. The respiratory care apparatus comprises a top cover 256, a bottom cover 258 and a side panel 260. The top cover 256, the bottom cover 258 and the side panel 260 are external components and form housing for the respiratory care apparatus 200. The top cover 256 features a touch enabled LCD/LED screen 262 as a user interface. The LCD/LED screen 262 enables a user to communicate with the respiratory care apparatus 200. The respiratory care apparatus 200 is configured to be operated on electrical power. Hence, a power button 264 and DC power input jack are provided externally for ease of access. A foot switch port 266 is provided at the bottom cover 258 of the respiratory care apparatus 200. A buzzer 268 is also provided to notify a care giver/patient/clinician about multiple events related to therapy such as data reception, data delivery, therapy completion, therapy schedule, and the like.

FIG. 5 illustrates a 3-D view of the respiratory care apparatus 200 in accordance with an embodiment of the present subject matter. In addition to the components described earlier, further components are shown in FIG. 5. The respiratory care apparatus 200 further comprises a silencer 270 and a battery 272. The silencer 270 is configured to control the noise due to the pressure generating sources. The battery 272 is provided to operate the respiratory care apparatus 200 in portable mode without external electric supply.

Referring FIG. 6, an exploded view of the respiratory care apparatus 200 has been illustrated. In an embodiment, the first pressure restricting valve 214, the second pressure restricting valve 216, the first electromechanical motor 238, the second electromechanical motor 244 are butterfly type. A butterfly housing comprising a top cover 274 and a bottom cover 276 is provided to house the first pressure restricting valve 214, the second pressure restricting valve 216 respectively. In addition to above, the respiratory care apparatus further comprises a foot switch connector 278, a DC supply jack 280 and a main controller PCB 282. In an embodiment, the manifold/air router structure 246 is a Y-type manifold, as shown in FIG. 6.

Figure 7:
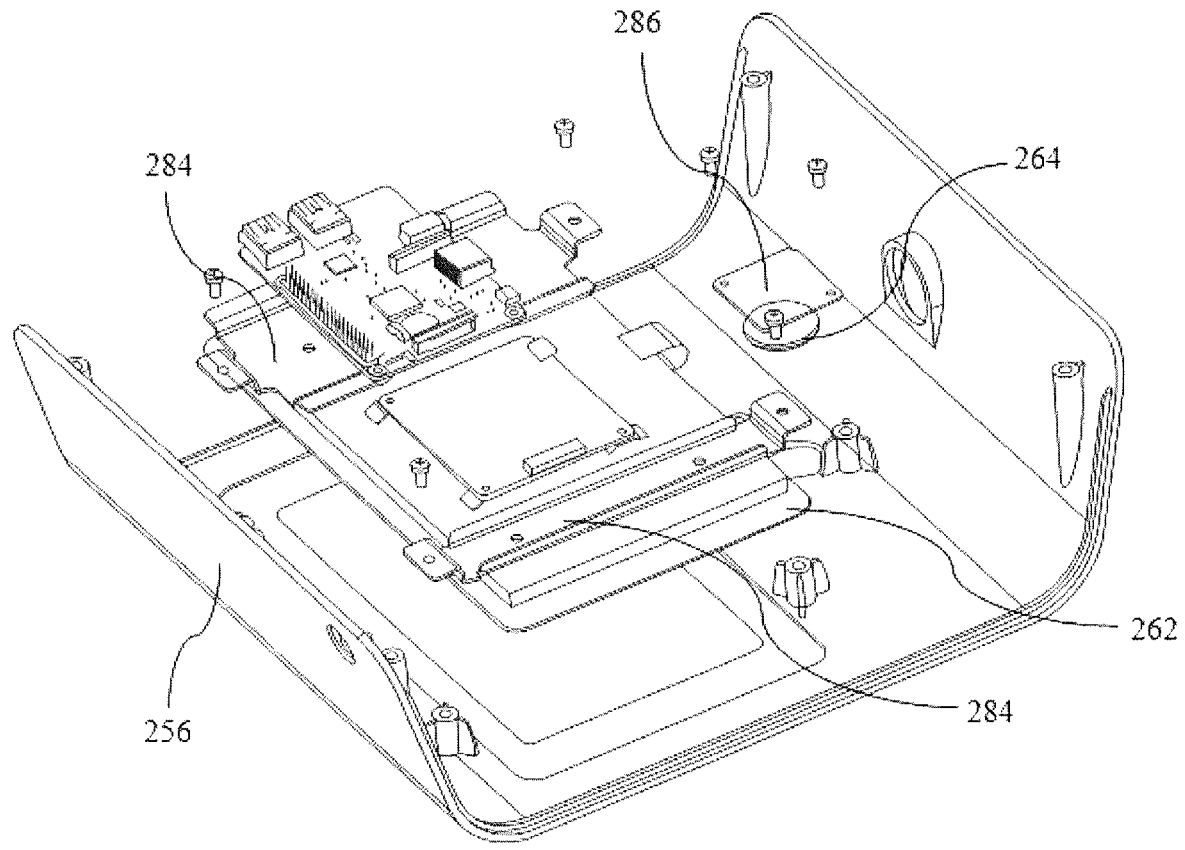
FIG. 7 illustrates an exploded view showing a top cover for the respiratory care apparatus and a display module according to an embodiment of the present subject matter.
Figure 8:
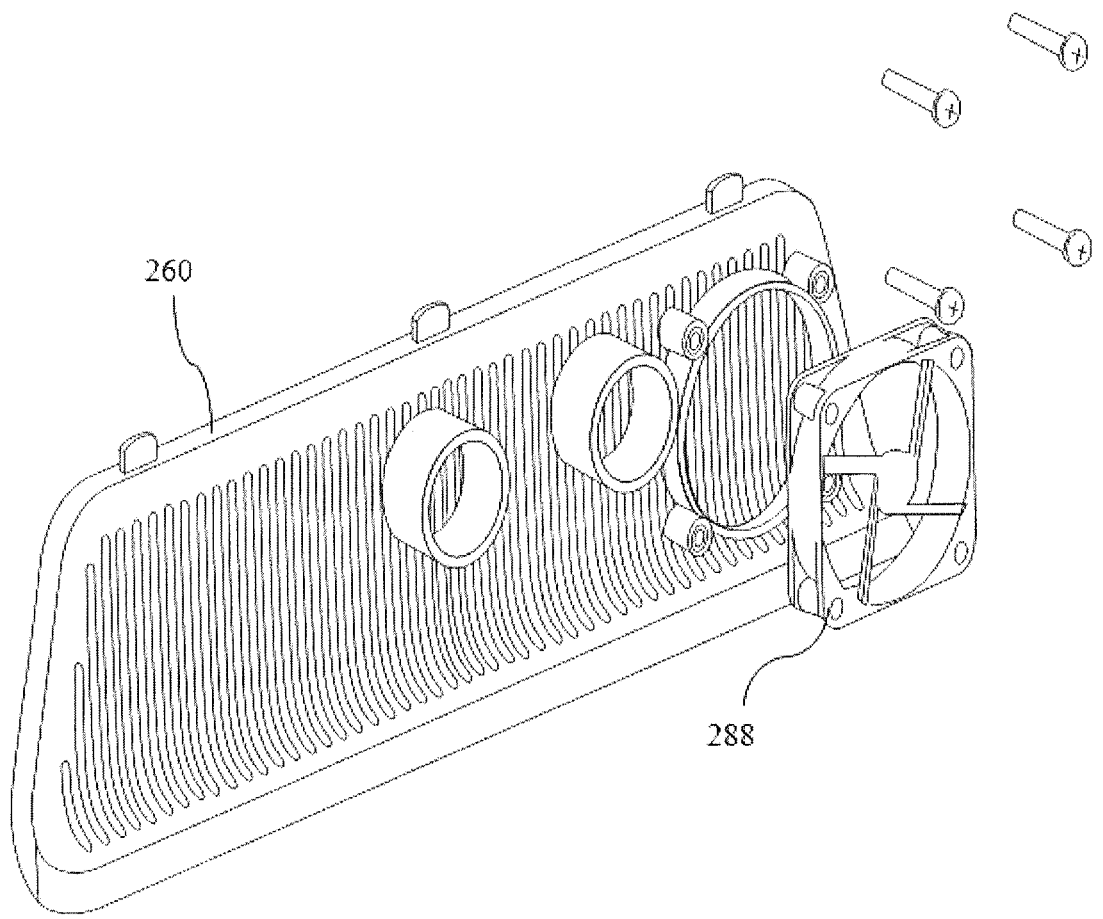
FIG. 8 illustrates an exploded view of a side panel and an exhaust fan for the respiratory care apparatus in accordance with an embodiment of the present subject matter.

As can be seen in FIG. 7, the top cover 256 and the touch enabled LCD/LED screen 262 are shown in an exploded view. At least one display mounting bracket 284 is provided to mount the touch enabled LCD/LED screen 262. Further, a power button PCB 286 is provided to enable the power button 264. Furthermore, an exhaust fan 288 is provided in proximity to the side panel 260. The side panel 260 and the exhaust fan 288 are illustrated in FIG. 8.

FIG. 9 illustrates the manifold/air router structure 246 in accordance with another embodiment of the present subject matter. A patient interface port 210 is shown along with two openings 290, 292 to be connected with the at least one first pressure generating source 206 and the at least one second pressure generating source 208.

In an embodiment, the electromechanical air router assembly (EARA) 202 is intelligently constructed in order to eliminate cross contamination, to provide precise positive and negative pressure, and to provide oscillatory functions during positive and negative cycles. Airway clearance therapies except nebulization such as HFCWO therapy, M-IE therapy, HFO/IPV therapy, PAP, oscillating PAP, suction, CPAP/CPEP and Bi-PAP are a combination of positive pressure, negative pressure and oscillation. Hence, EARA is suitable for a variety of airway clearance therapies. The different combinations of aforesaid positive pressure, negative pressure and oscillation are utilized to vary the type of therapy. Further, said variation is carried out with the help of the electromechanical valves placed in the first and second pneumatic/airway paths 250, 252 in respect of the flow generated by the at least one interfacing assembly 204 and the at least one second pressure generating source 208.

Figure 10:
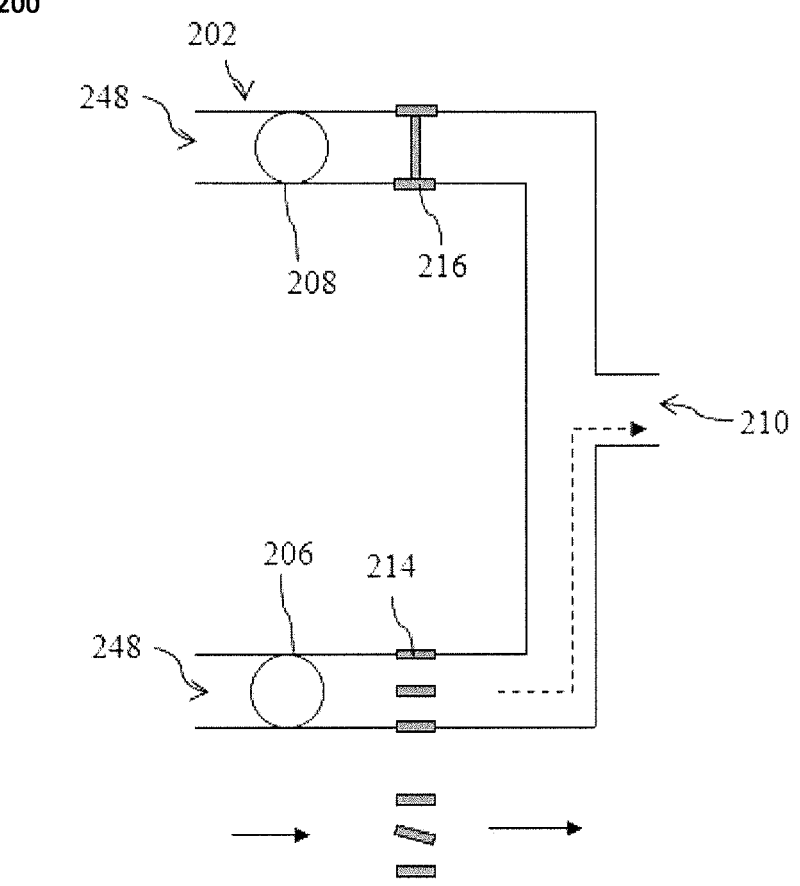
FIG. 10 is a schematic diagram of an electromechanical airway router assembly of a respiratory care apparatus illustrating a positive pressure generation mechanism in accordance with an embodiment of the present subject matter.
Figure 11:
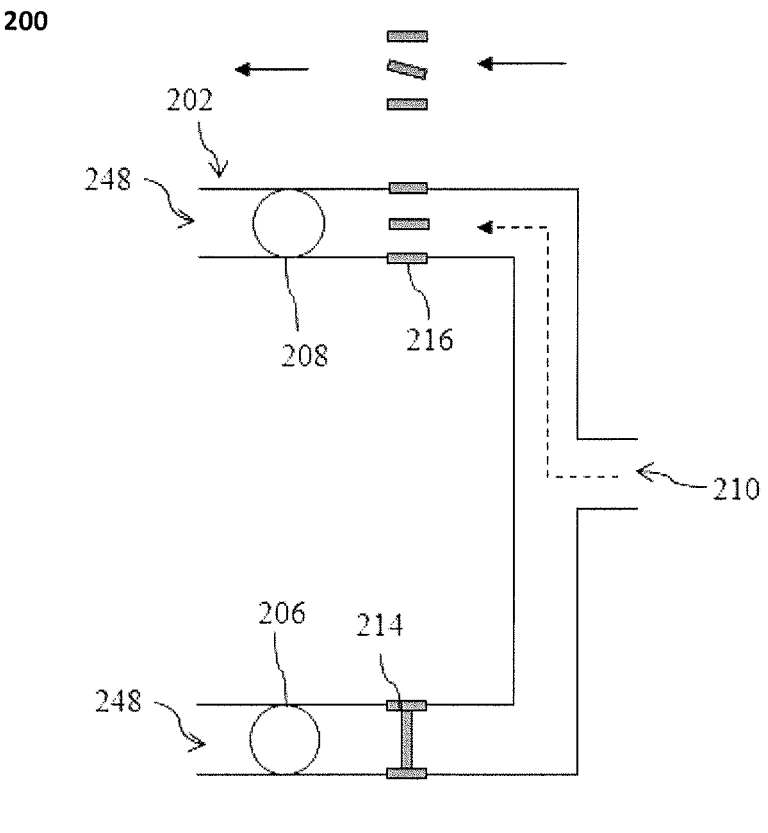
FIG. 11 is a schematic diagram of a electromechanical airway router assembly of a respiratory care apparatus illustrating a negative pressure generation mechanism in accordance with an embodiment of the present disclosure.

FIG. 10 & FIG. 11 illustrate mechanism for positive pressure generation and negative pressure generation respectively in accordance with an embodiment of the present subject matter. In operation, the at least one second pressure generating source 208 is blocked using the second pressure restricting valve 216 and the speed of the at least one interfacing assembly 204 is controlled in synchronization with the first pressure restricting valve 214. The pressure in the pneumatic/airway path is set to a value based on the feedback from one or more sensing parameters such as a pressure sensor, encoder, flow sensor, temperature sensor, and the like to create positive pressure at the at least one patient interface port 210. Similarly, the at least one interfacing assembly 204 is blocked using the first pressure restricting valve 214 and the speed of the at least one second pressure generating source 208 is controlled in synchronization with the second pressure restricting valve 216. The pressure is set to a value based on the feedback from one or more sensing parameters such as a pressure sensor, a flow sensor, a hall sensor, encoder, temperature sensor, and the like, to create negative pressure at the at least one patient interface port 210. Further, the at least one second pressure generating source 208 is blocked using the second pressure restricting valve 216 and the speed of the at least one interfacing assembly 204 is varied to generate oscillating waveform at the at least one patient interface port 210 and the first pressure restricting valve 214 is adjusted to generate positive waveform having a first amplitude value. The first pressure restricting valve 214 is further adjusted to generate a positive pressure having a second amplitude value. The oscillating pressure waveform thus generated, is based on user set parameters such as oscillation amplitude and oscillation pressure. The pressure at the at least one patient interface port 210 is controlled based on the feedback from one or more sensors such as pressure sensor, flow sensor, encoder, hall sensor, temperature sensor, and the like. The aforesaid positive waveforms can be continuous as well as discrete in nature with frequency ranging between 0 to 50

Hz. Furthermore, the at least one interfacing assembly 204 is blocked using the first pressure restricting valve 214 and the speed of the at least one second pressure generating source 208 is varied to generate oscillating waveform at the at least one patient interface port 210. The second pressure restricting valve 216 is adjusted to generate negative waveform having a first amplitude value. The second pressure restricting valve 216 is further adjusted to generate a negative pressure having a second amplitude value. The oscillating pressure waveform is generated based on user set parameters such as oscillation amplitude and oscillation pressure. The pressure at the patient interface port 210 is controlled based on the feedback from one or more sensors such as pressure, flow, encoder, hall sensor and temperature sensor. The aforesaid negative waveforms are continuous in nature with frequency ranging between 0 to 50 Hz.

In an embodiment, the first pressure restricting valve 214 and the second pressure restricting valve 216 can be used in synchronization with each other to generate oscillation simultaneously. The first pressure restricting valve 214 and the second pressure restricting valve 216 can be used in synchronization with each other to generate oscillation simultaneously. The at least one first pressure generating source 206 is unblocked using the first pressure restricting valve 214 such that the position of the first pressure restricting valve 214 is altered continuously from a first position to a second position. The at least one second pressure generating source 208 is partially unblocked using the second pressure restricting valve 216 such that the position of the second pressure restricting valve 216 is altered continuously from a first position to a second position. In other words, the at least one first pressure restricting valve 214 is in chopping state from an open position to achieve oscillations. Further, the position of the at least one second pressure restricting valve 216 is slightly changed from its closed position such that the second pressure restricting valve 216 begins to vibrate. Therefore, with such an arrangement, simultaneous oscillation/vibration at both the pressure restricting valves 214, 216 can be achieved. Further, The position of the first pressure restricting valve 214 and the position of the second pressure restricting valve 216 can be changed alternately to block/unblock the at least one first pressure generating source 206 and the at least one second pressure generating source 208 respectively to generate aggressive oscillation by forming alternate positive and negative waveforms.

In an embodiment, the respiratory care apparatus 200 further comprises a nebulizer connecting port for nebulization therapy and a sensor interfacing port in addition to the at least one patient interface port 210. The nebulizer can be pneumatic or electric in nature. The respiratory care apparatus 200 further comprises a bacterial filter and/or a viral filter for infection control. The respiratory care apparatus 200 also includes a built-in intelligence module configured to detect patient's breathing response to a frequency pressure waveform. The frequency range varies from 0 to 50 Hz. The intelligence module comprises a main control unit. The main control unit may comprise microcontrollers and/or microprocessors for controlling the functions of the respiratory care apparatus 200. The intelligence module is configured to process patient's response to oscillating waveform, the processing happens in time and frequency domain. Further, the processed data is used to assess parameters such as patient's lung condition and therapy performance. The intelligence module is configured to operate through a variety of other modules including but not limiting to driver module, platform module, therapy control module, interface manager and other control modules. The driver module includes blower driver, power circuitry driver, electronic motor valve driver, serial port drivers, fan driver, sensor drivers; pressure, flow, etc. The platform module includes positive pressure generator module, negative pressure generator module and oscillation generator module (electromechanical valve controller). The therapy control module includes nebulization generator module and therapy integration module which corresponds to the multiple airway clearance therapies associated with the respiratory care apparatus 200 of the present disclosure such as HFCWO therapy, M-IE therapy. HFO/IPV therapy, PAP, oscillating PAP, suction, CPAP/CPEP, Bi-PAP, and the like. The interface manager includes interface co-ordination with main communication controller and other modules. The other modules include power management, battery management, communication controller, heat/fan management, forced oscillation spirometry and alarm management.

Figure 13:
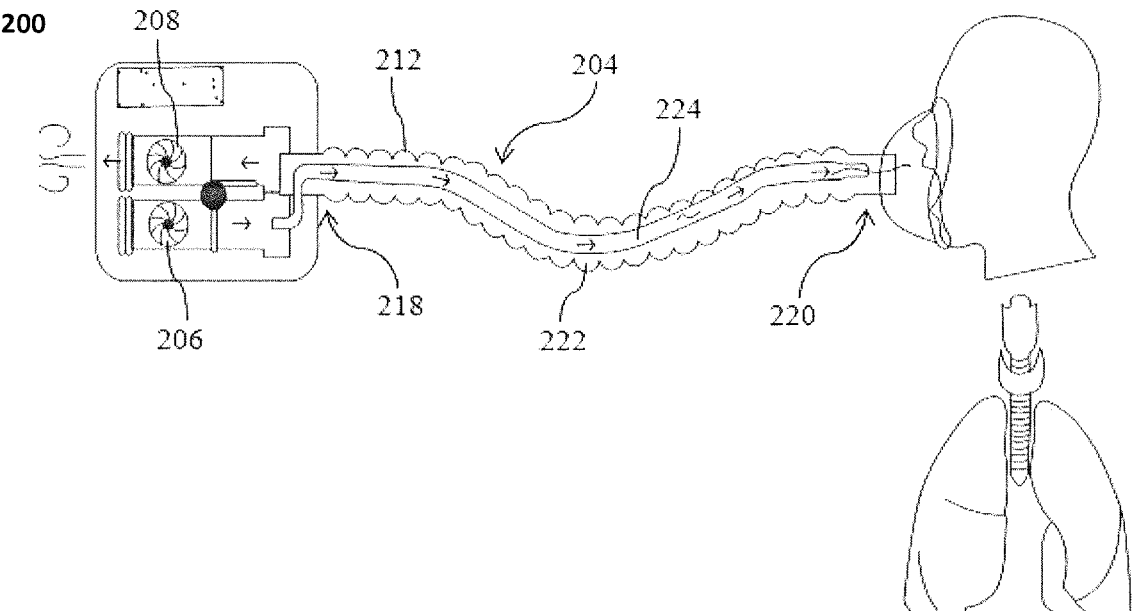
FIG. 13 is a schematic representation of a respiratory care apparatus showing a negative pressure generation and patient interface in accordance with an embodiment of the present subject matter.

Referring FIG. 12 & FIG. 13, a pictorial representation of positive pressure generation and negative pressure generation has been illustrated respectively. In a preferred embodiment, the patient interface tube 212 comprises a first end 218 and a second end 220. The first end 218 of the patient interface tube 212 is connected with the at least one patient interface port 210. The second end 220 of the patient interface tube 212 can be connected with a plurality of external members including but not limiting to a face mask, mouth piece, artificial lung tubing, tracheal tube adapter, expiratory resistance change adapter and ventilator interface adapter to provide the aforementioned airway clearance therapies. The patient interface tube 212 is tube-in-tube type having an outer conduit 222, an inner conduit 224 and a collector chamber. The inner conduit 224 can be used for inhalation and the outer conduit 222 can be used for exhalation and vice-versa. The collector chamber is configured to store the mucus/cough excreted by the patient during said therapy. The outer conduit 222 includes a suction chamber designed to trap the secretions such that the negative pressure/suction port in the collection chamber which is at higher position with respect to the portion of the patient interface tube 212 towards the patient end in order to reduce back flow of the secreted mucus/cough. The collection chamber itself acts as reservoir of negative pressure for exsufflation. The patient interface tube 212 comprises separate conduits for inhalation and exhalation to reduce contamination and infection.

Figure 14:
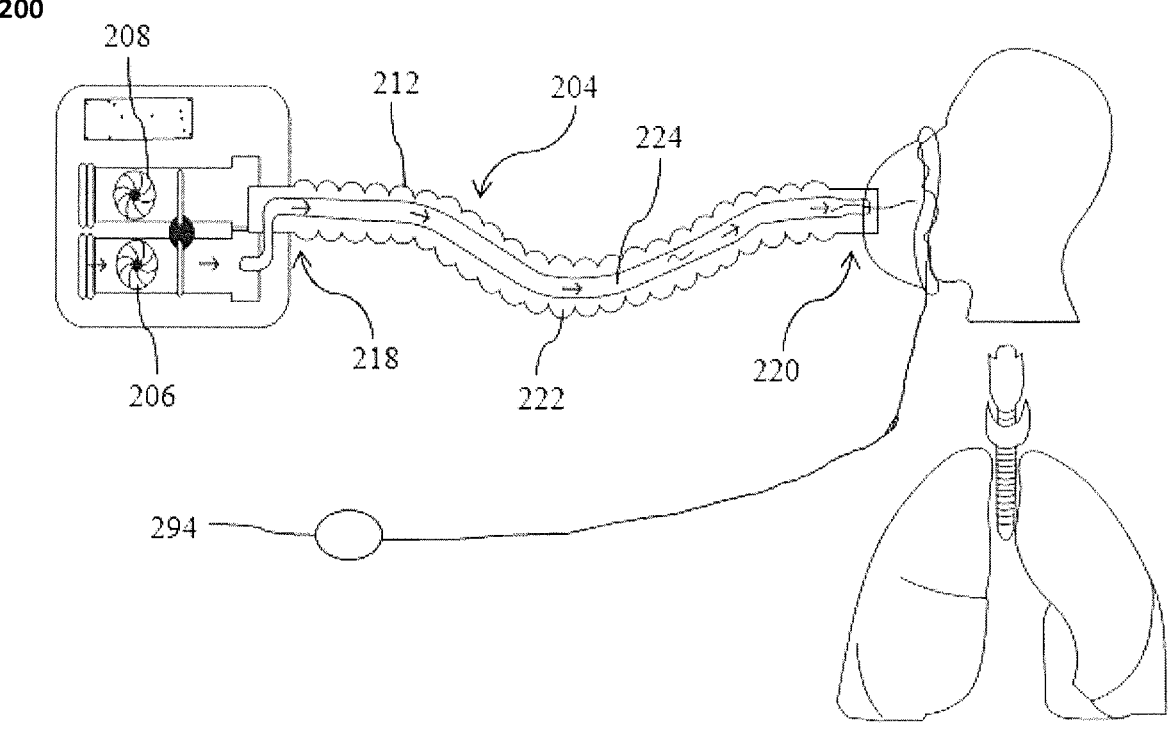
FIG. 14 is a schematic representation of a respiratory care apparatus showing a pressure generating source to deliver aerosolized medicine in accordance with an embodiment of the present subject matter.

FIG. 14 shows a pictorial representation of aerosolized medicine delivery through a pressure generating source. In an embodiment, the respiratory care apparatus 200 comprises a third pressure generating source 294. The third pressure generating source 294 is electrically/pneumatically driven. The aerosolized medicine is delivered to the patient through the third pressure generating source 294. Further, a control mechanism to deliver nebulization in synchronization with assisted inhalation and assisted exhalation cycle of the patient is also provided. The synchronization includes electronic control of the at least one third pressure generating source 294 at the same time with EARA operations.

FIG. 15a and FIG. 15b illustrate a schematic view of a patient garment 296 and a pressure generation mechanism of the respiratory care apparatus 200 respectively in accordance with an embodiment of the present subject matter. The interfacing assembly 204 further comprises a patient interface means (not shown) in connection with patient's external garment 296. The patient garment 296 includes two patient ports P1 and P2 connected with the patient interface means. The patient garment 296 expands during positive pressure generation and contracts during negative pressure generation. The mechanism for positive and negative pressure generation is explained above. The patient garment 296 oscillates due to alternate positive and negative pressure generation (as in the case of aggressive oscillation) and provides therapy to the patient. The patient interface means acts as a medium between the at least one patient interface port 210 and the external chest garment 296 of the patient to provide HFCWO (High Frequency Chest Wall Oscillation therapy).

The oscillation generation process includes simple oscillation (chopping) generation and aggressive oscillation generation. In case of simple oscillation generation, positive pressure path is intercepted based on the frequency of pressure restricting valve switching. The extent to which the pressure restricting valves 214, 216 open corresponds the amount of pressure generated and the flow delivered to the patient interface port 210. In other words, by changing the speed (rotations per minute) of the pressure generating sources and position of the pressure restricting valves 214, 216, additional control over pressure and flow of oscillatory waveform can be achieved. Further, in aggressive oscillation generation switching between the positive pressure generator and negative pressure generator helps to generate oscillatory waveform. Such an approach of oscillation generation is more aggressive and hence, more variation in flow/pressure can be achieved in lesser time using this approach. Extent to which the pressure restricting valves open decides the amount of pressure generated and the flow delivered to the patient. Additionally, by changing speed of the pressure generating sources 206, 208, additional control over pressure and flow of the oscillatory waveform can be achieved in this process.

The respiratory care apparatus 200 further comprises a connectivity module configured to transfer data. The connectivity module is based on LTE (Long Term Evolution) and GSM (Global System for Mobile Communications). The connectivity module comprises means for sending and receiving data, a display and other driver modules to enable the data transmission. The data transferred from the respiratory care apparatus 200 through the connectivity module comprises a plurality of parameters including but not limiting to delivered pressure, flow, pressure/flow related graphs and the corresponding user parameters. The data transferred using the connectivity module further comprises total device usage data, prescribed total therapy protocol, sensor data such as SpO2, respiratory rate, and the like. Further, the prescribed total therapy protocol comprises parameters such as possible pressure settings, oscillation settings, duration of therapy and number of therapies. The connectivity module comprises two way data communication enabling data transmission as well as data reception. The two way data communication comprises notes from individual such as patients, caregivers and clinicians, and the like. Further, the connectivity module is configured to provide assistance to the caregiver or patient regarding usage of interfacing assembly when switching from one type of airway clearance therapy to other.

As described hereinabove, the respiratory care apparatus 200 of the present subject matter provides a unique opportunity to address the pressing problems such as reducing the cross contamination and re-contamination. Further, the respiratory care apparatus 200 can deliver multitude of therapies in one footprint, hence, it helps to reduce cost burden to hospitals and caregivers, and enhances usability by reducing the footprints and simple intuitive user interface.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore, contemplated that such modifications can be made without departing from the spirit or scope of the present invention as defined.

What is claimed is:

1. A respiratory care apparatus comprising:
an electromechanical air router assembly comprising a first pressure generating source and a second pressure generating source;
an interfacing assembly having a patient interface port;
a first pressure restricting valve configured to control positive pressure and/or flow;
a second pressure restricting valve configured to control negative pressure and/or flow; and
a control mechanism,
wherein:
the first pressure generating source is configured to generate positive flow and pressure, the first pressure generating source comprises an inlet which is configured to draw atmospheric air into the first pressure generating source and an outlet which is configured to output air from the first pressure generating source to the patient interface port,
the second pressure generating source is configured to generate negative flow and pressure, the second pressure generating source comprises an inlet which is configured to draw air from the patient interface port into the second pressure generating source and an outlet which is configured to output air to atmosphere,
the interfacing assembly comprises a patient interface tube having a first end and a second end,
the first pressure generating source and the second pressure generating source are configured to function independently with respect to each other, the patient interface tube comprises separate conduits for inhalation and exhalation,
the electromechanical air router assembly is configured to provide separate inhalation and exhalation paths through the electromechanical air router assembly and the interfacing assembly,
the control mechanism comprises a microprocessor and one or more drivers, and
the control mechanism is configured to vary a speed of at least one of (i) the first pressure generating source or (ii) the second pressure generating source is to generate an oscillating pressure waveform at the patient interface port; and
the control mechanism is configured to control the first pressure restricting valve and the second pressure restricting valve in synchronization with speeds of the pressure generating sources to generate oscillation.

2. The respiratory care apparatus of claim 1, wherein the interfacing assembly is configured to be coupled with an external garment of a patient.

3. The respiratory care apparatus of claim 1, wherein:
the first pressure restricting valve is disposed between the first pressure generating source and the patient interface port, and the first pressure restricting valve is configured to control pressure between the first pressure generating source and the patient interface port, and the second pressure restricting valve is disposed between the second pressure generating source and the patient interface port, and the second pressure restricting valve is configured to control pressure between the second pressure generating source and the patient interface port.

4. The respiratory care apparatus of claim 1, wherein the first pressure restricting valve comprises a first electromechanical valve structure housed in a hollow structure having a first port and a second port.

5. The respiratory care apparatus of claim 4, wherein the first port is pneumatically connected to the outlet of the first pressure generating source and the second port is pneumatically connected to the patient interface port.

6. The respiratory care apparatus of claim 4, wherein the first electromechanical valve structure is configured to be controlled bi-directionally through displacement of a first electromechanical motor.

7. The respiratory care apparatus of claim 1, wherein the second pressure restricting valve comprises a second electromechanical valve structure housed in a hollow structure having a first port and a second port.

8. The respiratory care apparatus of claim 7, wherein the first port is pneumatically connected to the patient interface port and the second port is pneumatically connected to inlet of the second pressure generating source.

9. The respiratory care apparatus of claim 7, wherein the second electromechanical valve structure is configured to be controlled bi-directionally through displacement of a second electromechanical motor.

10. The respiratory care apparatus of claim 7, wherein the second electromechanical valve structure is in pneumatic connection with the atmosphere through the second pressure generating source.

11. The respiratory care apparatus of claim 7, wherein the second electromechanical valve structure is disposed in proximity with the inlet of the second pressure generating source.

12. The respiratory care apparatus of claim 1, further comprising a nebulizer connecting port and a sensor interfacing port.

13. The respiratory care apparatus of claim 1, further comprising:

a connectivity module configured to transfer data, wherein the connectivity module is based on LTE (Long Term Evolution) and GSM (Global System for Mobile Communications), wherein:

data transferred from the respiratory care apparatus through the connectivity module comprises one or more of delivered pressure, flow, pressure/flow related graphs, and related user parameters, data transferred from the respiratory care apparatus through the connectivity module comprises one or more of total device usage data, prescribed total therapy protocol, and sensor data selected from the group consisting of SpO2 and respiratory rate, the prescribed total therapy protocol comprises parameters selected from the group consisting of pressure settings, oscillation settings, duration of therapy, and number of therapies, and the connectivity module comprises two way data communication comprising notes from individuals selected from the group consisting of patients, caregivers, and clinicians.

14. The respiratory care apparatus of claim 1, wherein the microprocessor and one or more drivers are configured to deliver nebulization in synchronization with an assisted inhalation and assisted exhalation cycle of a patient.

15. The respiratory care apparatus of claim 1, wherein:

the patient interface tube is of a tube-in-tube type having an outer conduit and an inner conduit and coupled to the patient interface port, the outer conduit is pneumatically connected to the first pressure restricting valve, and the inner conduit is pneumatically connected to the second pressure restricting valve.

16. The respiratory care apparatus of claim 1, wherein the control mechanism is configured to:

control a speed of the first pressure generating source in synchronization with the first pressure restricting valve, and control a speed of the second pressure generating source in synchronization with the second pressure restricting valve.

\* \* \* \* \*